US00PP29265P3

(12) United States Plant Patent
Silva

(10) Patent No.: US PP29,265 P3
(45) Date of Patent: May 1, 2018

(54) LEMON TREE NAMED 'SILVA'S SEEDLESS'

(50) Latin Name: *Citrus limon*
Varietal Denomination: Silva's Seedless

(71) Applicant: Joe E. Silva, Orosi, CA (US)

(72) Inventor: Joe E. Silva, Orosi, CA (US)

( * ) Notice: Subject to any disclaimer, the term of this patent is extended or adjusted under 35 U.S.C. 154(b) by 55 days.

(21) Appl. No.: 14/999,489

(22) Filed: May 12, 2016

(65) Prior Publication Data

US 2017/0332531 P1 Nov. 16, 2017

(51) Int. Cl.
*A01H 5/08* (2018.01)

(52) U.S. Cl.
USPC ..... Plt./201

CPC ..... *A01H 5/0806* (2013.01)

(58) Field of Classification Search
USPC ..... Plt./201
See application file for complete search history.

*Primary Examiner* — Keith O Robinson
(74) *Attorney, Agent, or Firm* — Mark D. Miller

(57) ABSTRACT

A new and distinct variety of seedless lemon named 'Silva's Seedless' characterized by producing mature seedless fruit with thin rinds during early July in the San Joaquin Valley of California, thereby avoiding potential calamities from winter weather. The trees have small thorns, minimizing the need for protective equipment for growers, and have high yields and bear from year three onwards. The fruit is well sized and has acceptable acid-sugar ratios and color. The skin has a smooth texture and the fruit stores well. The fruit has an average juice content of 30-40% at harvest. The fruit shape is typically ovoid.

6 Drawing Sheets

BACKGROUND OF THE NEW VARIETY

The present invention refers to a new variety of lemon which will hereinafter be denominated as the 'Silva's Seedless' lemon tree. The 'Silva's Seedless' tree produces commercially seedless lemon fruit, maturing in early to mid-July in the central San Joaquin Valley of California. The 'Silva's Seedless' trees bear from year three, and have consistent year-to-year bearing habits. The fruit is seedless with thin rinds, acceptable acid-sugar ratios and color, and has an average juice content of 30-40% at harvest.

In the development of new commercial fruit varieties, specific characteristics provide a premium on those fruit varieties that mature early or late in the growing season. For a new fruit variety to be a commercial success, the fruit must be of good size, good color, and also have good holding/storage. Advantageous harvest times and shipping characteristics are also important, as is the date the fruit matures. This new invention meets all of the aforementioned criteria and therefore would be of commercial appeal to the consumer.

ORIGIN AND ASEXUAL REPRODUCTION OF THE NEW VARIETY

The invention (variety) comprises a new and distinct variety of a seedless lemon plant named 'Silva's Seedless' discovered by the inventors in Orosi, Calif. in 2010. The new invention is a graft of a 'Persian' lime (unpatented) onto a 'Eureka' lemon (unpatented) scion having a 'Volkameriana' (Volker, unpatented) rootstock. The new invention was subsequently asexually reproduced by the inventors in 2012 by bud grafting on to 'Volkameriana' root stock. The resulting trees were thereafter evaluated and compared with the parent trees, including the fruit, and have been found to be identical in all respects. The trees under evaluation are free from all known viruses and viroids including; *Tristeza, Exocortis, Xyloporosis* and *Psorosis*.

In comparison to the parent varieties, the fruit of the present variety has more juice than that of the 'Persian' lime, but less flesh than 'Persian' lime. The fruit of the present variety has a thin rind with a shiny surface, that is similar to the 'Persian' lime. The fruit of the present variety has a thicker rind than that of the 'Eureka' lemon, with a shinier surface than the 'Eureka' lemon.

SUMMARY OF THE NEW VARIETY

The 'Silva's Seedless' is particularly characterized by producing seedless fruit with thin rinds that matures between approximately July 5-July 15 in a normal year, with good fruit size and stable year-to-year yields. The trees are also characterized by having small thorns of between ⅛ inch to ¼ inch in length, minimizing the need for protective equipment for growers.

DETAILED DESCRIPTION

Referring more specifically to the horticultural details of the new and distinct variety of triploid lemon, the following descriptions have been observed under the ecological conditions prevailing at the origin orchard which is located in Orosi, Calif. Color references are to the Dictionary of Color by Maerz and Paul, First Edition published in 1930. Common colors are also employed.

Tree:

*Size*.—Medium, for 3rd year tree. Height: 4-5 feet. Width: 3 feet at drip line.

*Shape*.—Upright growth habit when grown on 'Volkameriana' rootstock.

*Growth*.—Dense; vigorous branches tend to grow out, upward beyond trees' general periphery; abundant axillary and accessory bud development.

*Vigor*.—Strong.

*Productivity*.—Very good for $3^{rd}$ year tree with regular bearing; fruit produced predominantly inside the canopy resulting in less fruit scarring.

Trunk: Immediately above the rootstock interface on 'Volkameriana':

*Size*.—Circumference of 160-200 mm (6.28-7.85 inches), approx. 18 inches above ground.

*Surface texture*.—Smooth.

*Color*.—3 year old tree, gray [5-A-7].

*Lenticels*.—Approximately 20 per square inch.

Branches:

*Size*.—Scaffold (structural) branches, circumference of 60-80 mm (2.36-3.15 inches); Secondary branches (on which fruit bearing branches are borne) circumference of 12-20 mm (4.72-7.87 inches).

*Length of branches*.—Variable, between 5 and 36 inches; average length 18-24 inches.

*Angle of branches*.—Average of 75 degrees, between about 30 degrees and about 90 degrees.

*Color of branches over* 2 *years old*.—Brunswick green [22-L-10], striped with and becoming solidly gray [5-A-7].

*Color of branches less than* 2 *years old*.—Brunswick green [22-L-10].

Figure 1:
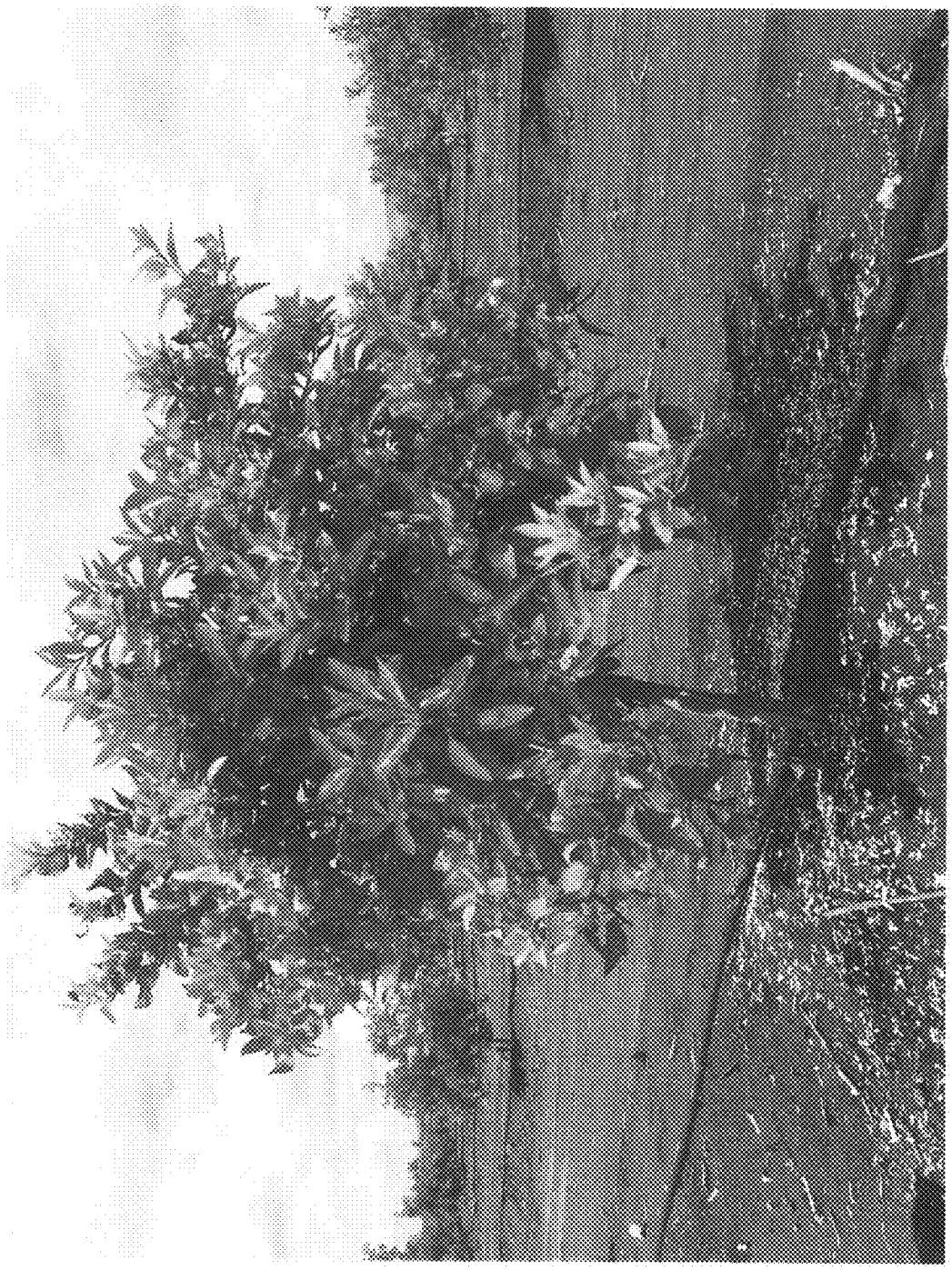
FIG. 1 is a color photograph of a typical three year old tree.
Figure 2:
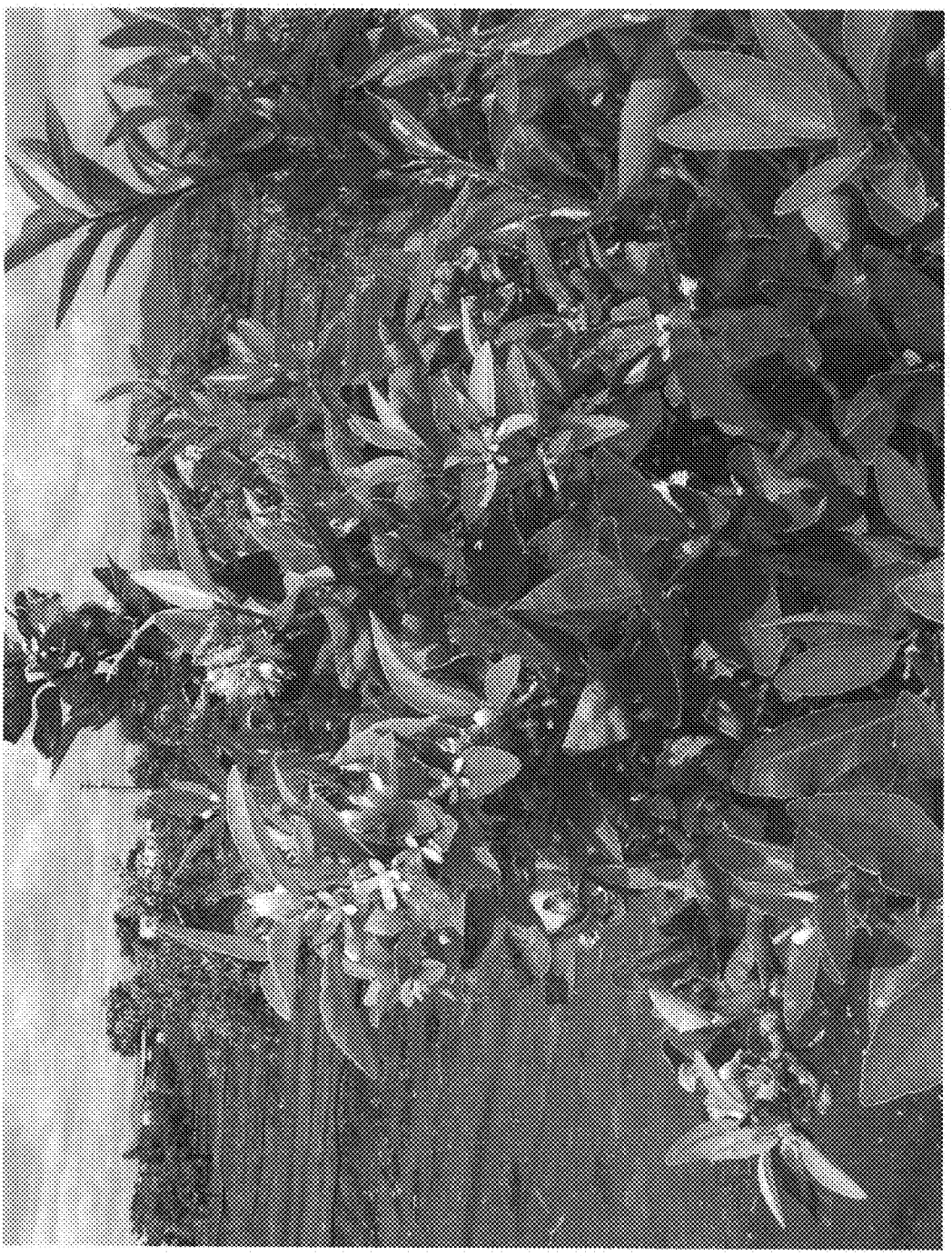
FIG. 2 is a color photograph of a portion of a three year old tree, showing a typical view of flowers of the present invention.
Figure 3:
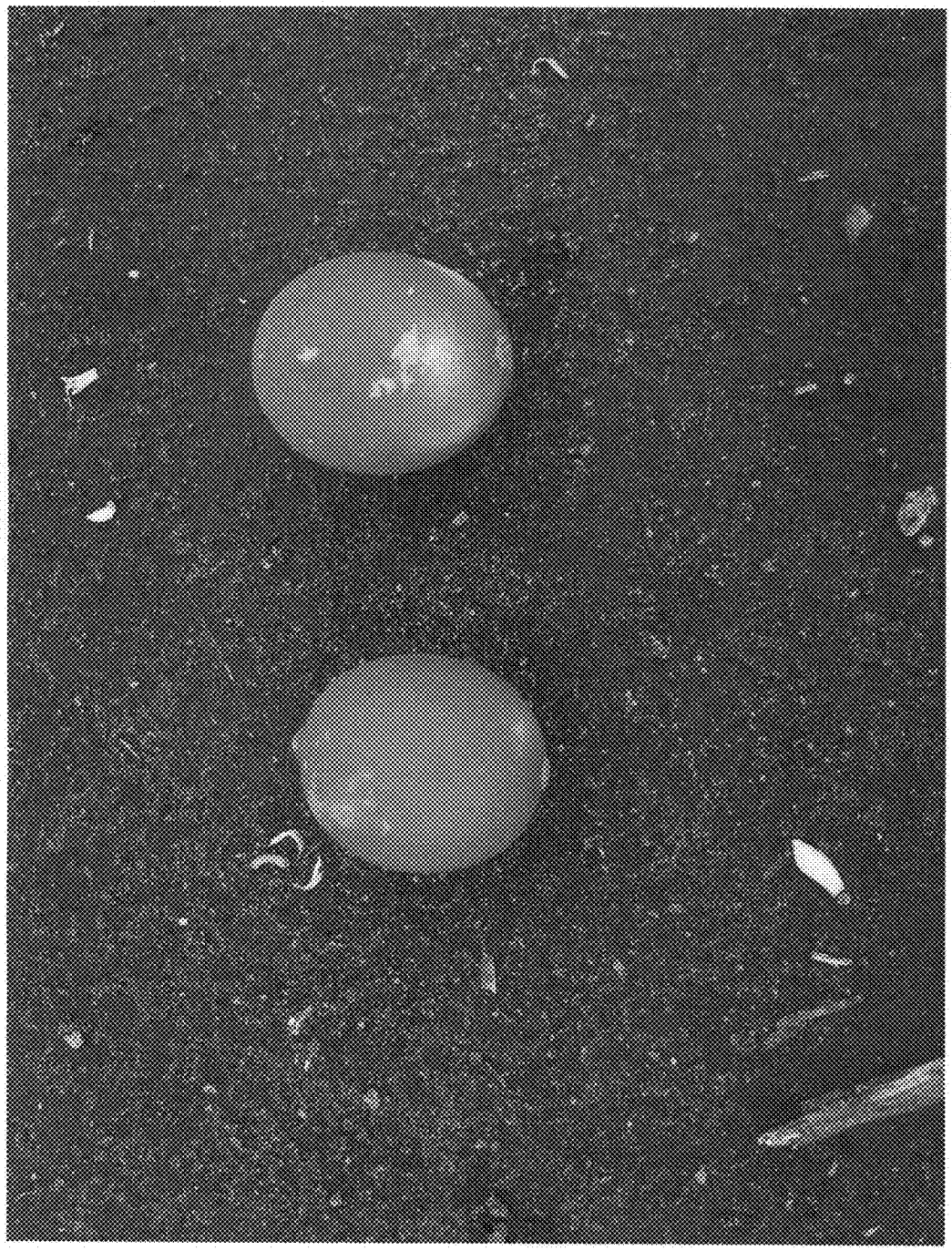
FIG. 3 is a color photograph showing perspective views of two specimens of typical whole fruit of the present invention harvested in the spring of 2016.
Figure 4:
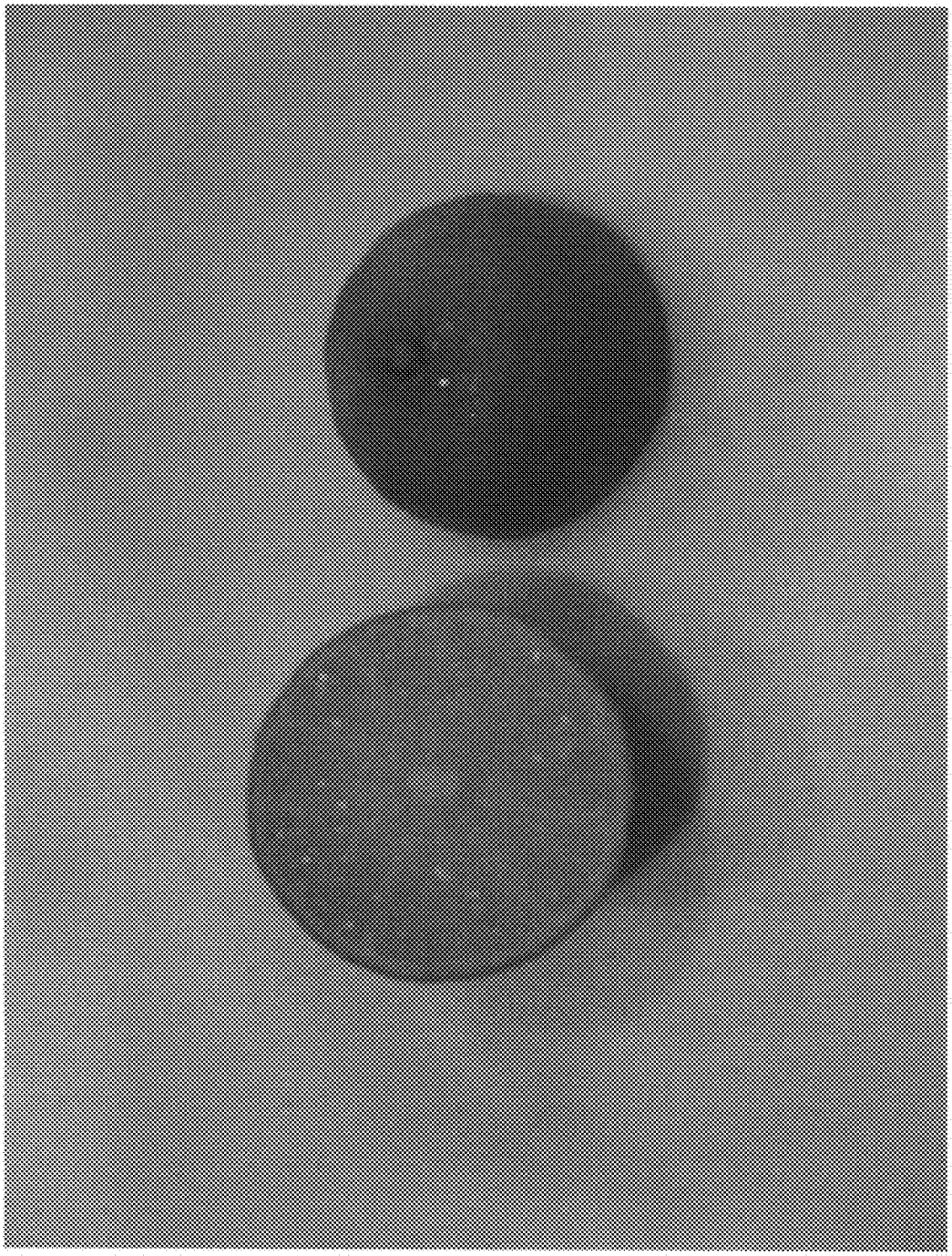
FIG. 4 is a color photograph of transversely cut fruit of the present invention harvested in the spring of 2016.
Figure 5:
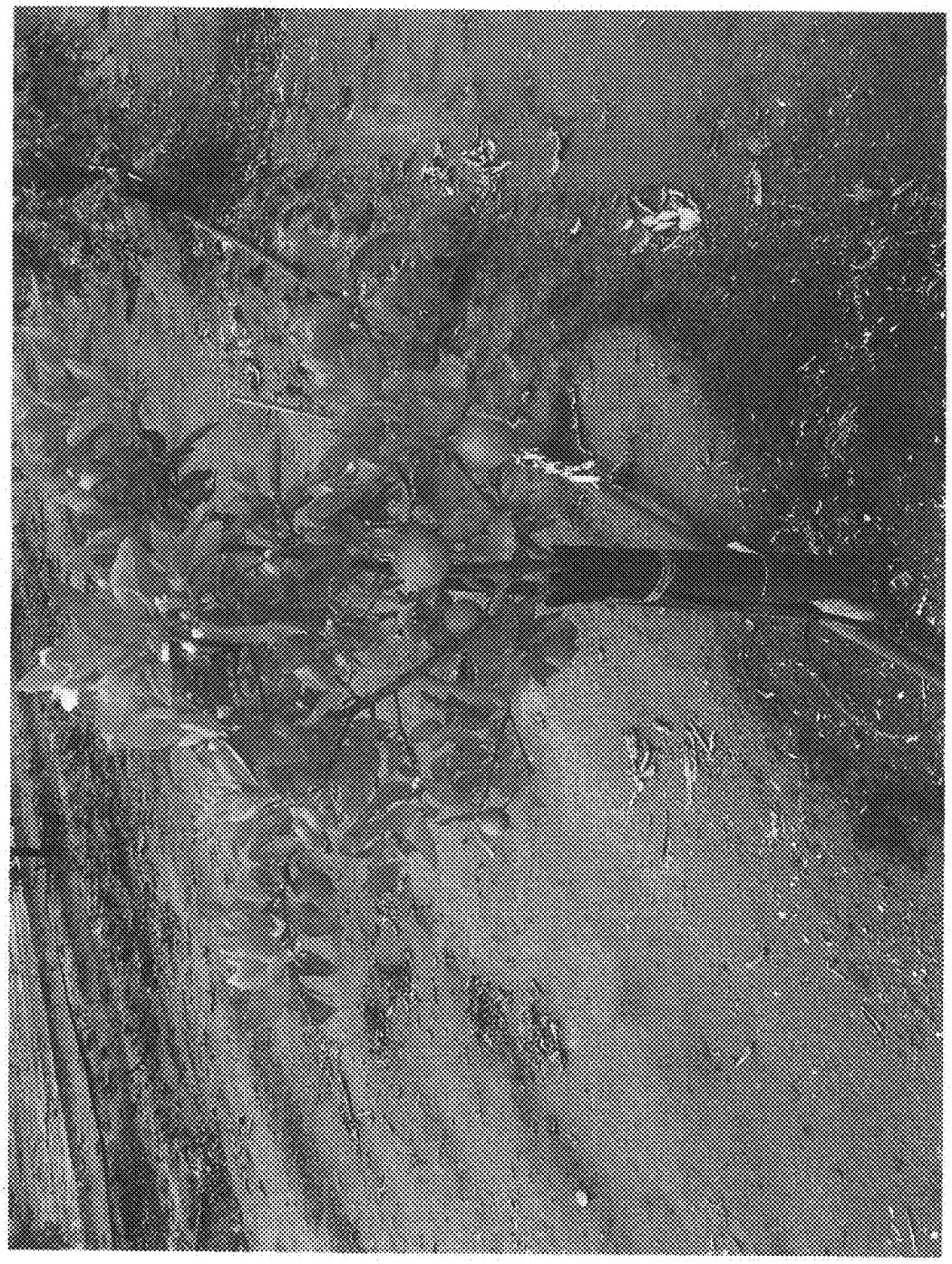
FIG. 5 is a color photograph showing a three year old tree with fruit.
Figure 6:
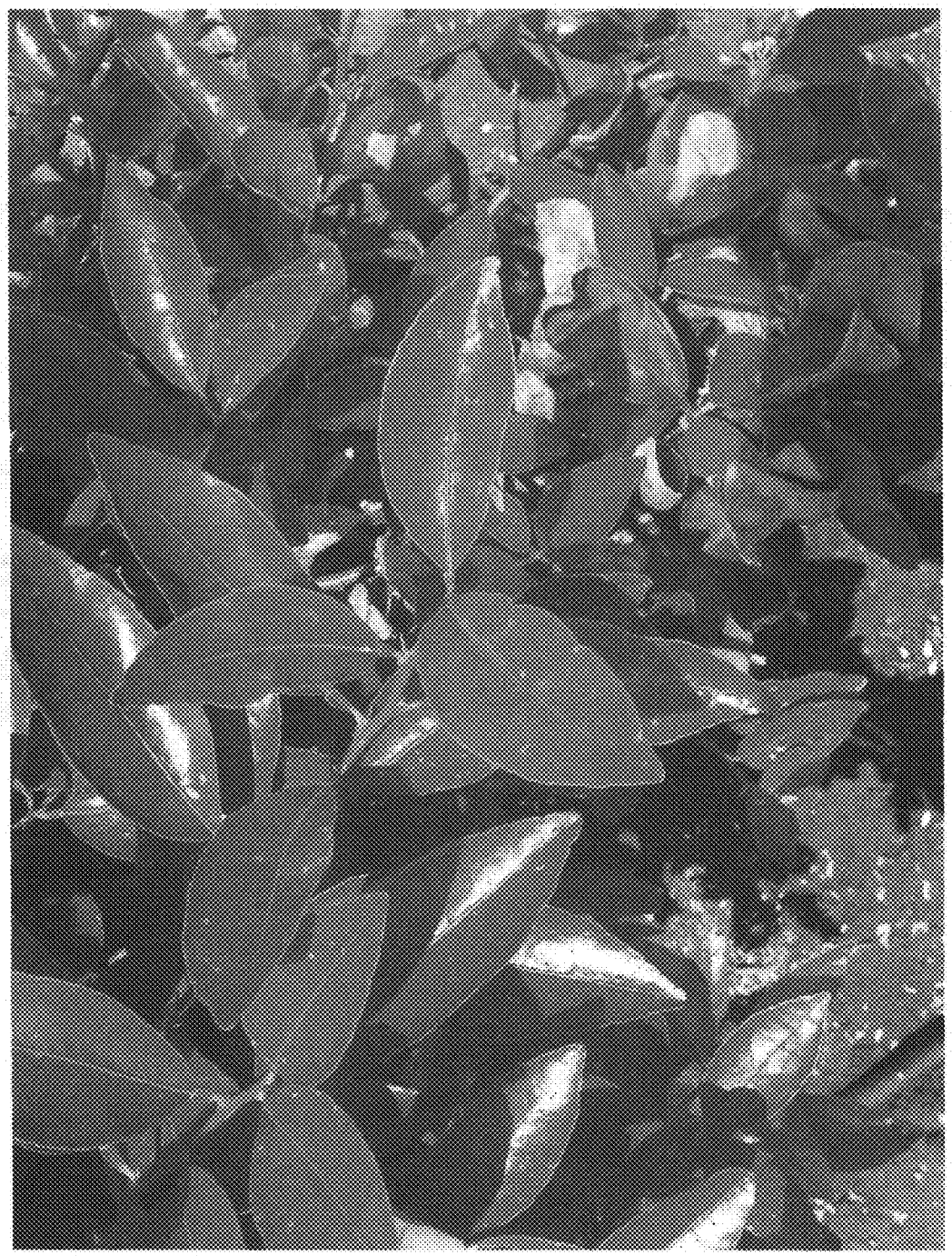
FIG. 6 is a color photograph of branches from a three year old tree, showing the typical leaf arrangement and small thorns of the present invention.

*Thorns*.—Small, 3-6 mm (0.12-0.24 inches) (See FIG. 6.).

Leaves: The leaves are alternate, unifoliate with distinct articulation between the petiole and leaf blade. They exhibit a slight to strongly curvate morphology, and have small basal wings.

*Size*.—Medium.

*Length*.—59-97 mm (2.32-3.82 inches).

*Width*.—19-54 mm (0.75-2.13 inches).

*Texture*.—Predominantly smooth adaxially to slightly pebbled abaxially, veins on the adaxial and abaxial surface very slightly raised, except for the midvein, which is prominently raised on both sides of the leaf.

*Shape*.—Elliptically oval to oblong. Approximately transversely and longitudinally symmetrical.

*Margin*.—Crenate, with rounded serrations at edge.

*Apex*.—Mild crenation to pointed at the apex (mildly acute).

*Base*.—Not elongated.

*Edges*.—Distinctly smoother towards the basal leaf end.

*Marginal oil cells*.—Many, 10-15 per linear cm; oil cells are ovoid and smooth.

*Anthocyanin coloration in the young leaves*.—Absent.

*Color*.—Mature leaves glossy. Upper surface — green [22-L-9 to 23-L-10]. Lower surface — Piquant green [20-K-6].

*Petioles*.—Length: 7-13 mm (0.28-0.51 inches). Diameter: around 2 mm (0.08 inches). Wings: 1-1.5 mm (0.04-0.06) wide on either side of petiole, at widest point. Color: Brunswick green [22-L-10] to [23-L-9].

*Venation*.—Distinct, pinnately reticulated.

*Midvein*.—Width at base, 0.9-1 mm (0.035-0.04 inches); Width at apex, 0.2-0.3 mm (0.008-0.012 inches). Color: Brunswick green [22-L-10].

Flowers: The flowers are large and complete. Flower buds have very slight anthocyanin coloration during early development, but lose this pigmentation by anthesis. Flowers are borne in single or multiple clusters and have an average number of stamens (about 20) with complete style development. Anther color is very pale tan to yellow. The flowers have a sweet pleasing citrus fragrance.

*Flower buds*.—Shape: 10 days prior to anthesis, slightly ovoid, 5 mm (0.20 in.) diameter; 1-2 days prior to flowering, elongated cone, 7-8 mm (0.28-0.31 in.) diameter. Length: 8-16 mm (0.31-0.63 inches).

*Calyx*.—4-5 sepals, fused forming a cup-like calyx. Color: Russet green [20-K-1] to [20-K-3]. Lobe tips are blunt but with apiculate tips.

*Date of normal first bloom*.—In Orosi, Calif.: First bloom about March 10th, end bloom about April $10^{th}$.

*Flowers*.—Medium — in clusters of three to five. Diameter when fully opened: 19-28 mm (0.75-1.10 inches). Bloom: e.g. quantity — abundant (typical of a lemon) non-alternate bearing.

*Petals*.—4-5, acute tips. Size: medium to large (compared to other citrus species). Length: 15-18 mm (0.59-0.71 inches). Width: 4-5 mm (0.16-0.2 inches). Form: narrow, linear, slightly oblong. Color: Adaxial surface — white [1-A-1]. Abaxial surface — off-white [9-B-1] to slightly pink [2-B-1]. Claws: none. Petal Margins: smooth, pointed at tips (acute).

*Pedicel*.—3-5 mm (0.12-0.2 inches). Color: light green [19-L-7].

*Sepals*.—Color: Russet green [20-K-1 to 20-K-3].

*Stamen*.—Number: approx. 20. Length 10-12 mm (0.39-0.47 inches). Filament: white (10-A-1). Anthers: Length: 1.5-3 mm (0.06-0.12 inches). Width: 0.5-1 mm (0.02-0.04 inches). Color: light tan [10-D-2].

*Pistil*.—Stigma: ovoid shape, 1.5-2.5 mm (0.06-0.1 in.) diameter; Color: Chartreuse [11-L-1]. Style: Length: 3-4 mm (0.12-0.16 inches). Width: 1-2 mm (0.04-0.08 inches). Color: light sea green [19-F-2]. Ovary: 2-3 mm (0.08-0.12 inches) diameter; ovoid shape; Color: green [22-L-9].

Fruit: On grafted trees the first fruit production occurred after two seasons. Internal characteristics: The fruit is commercially seedless in its normal cropping cycle. There is no persistence of the style on the fruit.

Internal characteristics:

*Flesh color*.—Near rind, yellow-green [18-J-3]. Remainder, yellow-green [18-J-3].

*Interior segments*.—Average of 8 to 10 in number.

*Interior segment membranes*.—Thin.

*Pulp vesicles*.—Medium, 10-12 mm (0.39-0.47 in.) length; 2 mm (0.08 in.) diameter; color: yellow-green [18-J-3].

*The septa*.—Almost perfectly axile from center, no convexity or concavity.

*Seeds*.—None.

*Juice*.—Abundant in mature fruit, evenly distributed in sections, lemon-lime flavor, (pH of 2.6). The fruit center is complete without separation. Rind oil cells are medium to large, and occur at a density of approximately 60-100 per $cm^2$. The fruit rind is oily. Glandular layer 1-2 mm (0.04-0.08 inches). Mesocarp (albedo) 1-2 mm (0.04-0.08 inches).

*Axis*.—3-6 mm (0.12-0.24 inches) diameter.

*Date of maturity*.—In Orosi, Calif.: about July 5th-July $15^{th}$.

External characteristics:

*Size*.—Medium. Length: 50-70 mm (1.97-2.76 inches). Width: 40-55 mm (1.57-2.17 inches).

*Form*.—Ovoid, with the broadest part of the fruit at the middle. Fruit surface — smooth. Basal (stalk/stem end) slightly raised and puckered around calyx; no depression present.

*Neck*.—Absent.

*Base*.—Diameter 12-14 mm (0.48-0.56 inch).

*Calyx*.—Diameter 6-8 mm (0.24-0.31 inch).

*Apex*.—Slightly raised, slightly nippled.

*Nipple*.—Present, weakly prominent.

*Areole*.—Absent.

*Stylar scar*.—Slight, diameter 1 mm (0.04 inch).

*Rind*.—Surface — oily, smooth, medium glossiness present. Thickness — thin; average 2-4 mm (0.08-0.16 inch). Color: Yellow-green [19-L-8] at first harvest (July) developing to a light yellow-green by the end of September. The fruit can set without pollination. Internal fruit quality acceptability occurs approximately one month prior to color change. The above description of this new variety of lemon is based on the growing conditions prevalent in Orosi, Calif.; variations of the usual magnitude, such as differences in maturity date and production, may be due to cultural practices including irrigation, fertilization, pruning, fruit thinning and primary climate changes as well as soil conditions.

*Use*.—Fresh market/juice/oil extraction.

*Keeping quality*.—Excellent (stores for 6 month in controlled atmosphere).

*First harvest date*.—Around July $5^{th}$ in Orosi, Calif.

*The present variety has resistance to California red scale.—Aonidiella aurantii*. Post harvest disorders are similar to existing lemon varieties. In post harvest storage trials under standard controlled atmosphere conditions, the 'Silva's Seedless' could be economically stored, with minimal fruit loss for at least 6 months.

What is claimed is:

1. A new and distinct early harvesting variety of seedless lemon as described and illustrated called 'Silva's Seedless' that is characterized as producing seedless fruit with thin rinds that matures between approximately July $5^{th}$ and July $15^{th}$ in the San Joaquin Valley of California, the trees having small thorns and coming into bearing by year 3, consistently bearing each year thereafter, the seedless fruit having typically ovoid shape, an average juice content of about 30% to about 40% at harvest, with smooth skin texture, and having acceptable acid-sugar ratios and color.

* * * * *